US011579729B2

United States Patent
Choi et al.

(10) Patent No.: US 11,579,729 B2
(45) Date of Patent: Feb. 14, 2023

(54) DISPLAY DEVICE AND METHOD FOR OPERATING THE SAME

(71) Applicant: Samsung Display Co., Ltd., Yongin-si (KR)

(72) Inventors: Boram Choi, Asan-si (KR); Soojung Lee, Suwon-si (KR); Yuna Kim, Seoul (KR); Seungwook Chun, Daegu (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 17/357,813

(22) Filed: Jun. 24, 2021

(65) Prior Publication Data

US 2022/0283690 A1 Sep. 8, 2022
US 2022/0404947 A9 Dec. 22, 2022

(30) Foreign Application Priority Data

Sep. 24, 2020 (KR) .................. 10-2020-0124010

(51) Int. Cl.
*G06F 3/041* (2006.01)
*G06F 3/044* (2006.01)
*A61B 5/00* (2006.01)
*G06F 3/14* (2006.01)

(52) U.S. Cl.
CPC ......... *G06F 3/04186* (2019.05); *A61B 5/443* (2013.01); *A61B 5/6898* (2013.01); *A61B 5/742* (2013.01); *G06F 3/0446* (2019.05); *G06F 3/14* (2013.01); *G06F 3/044* (2013.01); *G06F 2203/04112* (2013.01)

(58) Field of Classification Search
CPC .. G06F 3/04186; G06F 3/0446; G06F 3/0488; G06F 2203/04112; G06F 3/044; A61B 5/443; A61B 5/6898; A61B 5/742
USPC ..................................................... 345/174
See application file for complete search history.

(56) References Cited

U.S. PATENT DOCUMENTS

| | | | | |
|---|---|---|---|---|
| 6,730,863 B1 * | 5/2004 | Gerpheide | ............ | G06F 3/0445 345/174 |
| 8,273,021 B2 | 9/2012 | Jang et al. | | |
| 8,652,042 B2 * | 2/2014 | Mattoli | ............... | A61B 5/0537 600/306 |
| 10,181,021 B2 | 1/2019 | Venkatraman et al. | | |
| 11,171,185 B2 * | 11/2021 | Kim | ...................... | G06F 3/0443 |
| 2005/0159655 A1 * | 7/2005 | Kao | ......................... | A61B 5/442 600/306 |
| 2015/0156298 A1 * | 6/2015 | Ikemoto | ............ | H04M 1/72403 455/556.1 |
| 2016/0216812 A1 * | 7/2016 | Bermel | ................... | G06F 3/045 |
| 2019/0179448 A1 * | 6/2019 | Lim | ....................... | G06F 3/0446 |

(Continued)

FOREIGN PATENT DOCUMENTS

JP 2018-047223 3/2018
KR 10-0862287 10/2008

(Continued)

*Primary Examiner* — Tom V Sheng
(74) *Attorney, Agent, or Firm* — H.C. Park & Associates, PLC

(57) ABSTRACT

A display device includes a display panel, an input sensor, and a readout circuit. The display panel is configured to display an image. The input sensor is disposed on the display panel. The readout circuit is configured to output a moisture level signal corresponding to sensing signals received from the input sensor in a skin measurement mode.

20 Claims, 15 Drawing Sheets

(56) References Cited

U.S. PATENT DOCUMENTS

| | | | |
|---|---|---|---|
| 2019/0220143 A1* | 7/2019 | Kim | G06F 3/0412 |
| 2019/0246976 A1* | 8/2019 | Howell | A61B 5/01 |
| 2020/0022275 A1* | 1/2020 | Vemulapally | G01K 1/14 |
| 2020/0124655 A1 | 4/2020 | Kim et al. | |
| 2021/0043693 A1* | 2/2021 | Kim | G06F 3/0443 |

FOREIGN PATENT DOCUMENTS

| | | |
|---|---|---|
| KR | 10-2019-0071032 | 6/2019 |
| KR | 10-2020-0045124 | 5/2020 |
| KR | 10-2020-0057533 | 5/2020 |

* cited by examiner

DISPLAY DEVICE AND METHOD FOR OPERATING THE SAME

CROSS-REFERENCE TO RELATED APPLICATIONS

This application claims priority to and the benefit of Korean Patent Application No. 10-2020-0124010, filed Sep. 24, 2020, which is hereby incorporated by reference for all purposes as if fully set forth herein.

BACKGROUND

Field

Embodiments generally relate to a display device, and more particularly, to a display device capable of sensing an external input.

Discussion

Multimedia electronic apparatuses, such as televisions, mobile phones, tablet computers, navigators, game consoles, and the like, typically include a display device for displaying an image. Such an electronic apparatus may include a display device capable of providing a touch-based input manner that allows a user to easily input information or commands intuitively and conveniently in addition to usual input manners, such as a button, a keyboard, a mouse, and the like. As personal electronic apparatus, such as mobile phones, smart watches, etc., become widely used, a need for a display device capable of providing biometric information is increasing.

The above information disclosed in this section is only for understanding the background of the inventive concepts, and, therefore, may contain information that does not form prior art.

SUMMARY

Some aspects provide a display device capable of providing skin moisture level information.

Some aspects provide a method of operating a display device capable of providing skin moisture level information.

Additional aspects will be set forth in the detailed description which follows, and, in part, will be apparent from the disclosure, or may be learned by practice of the inventive concepts.

According to an embodiment, a display device includes a display panel, an input sensor, and a readout circuit. The display panel is configured to display an image. The input sensor is disposed on the display panel. The readout circuit is configured to output a moisture level signal corresponding to sensing signals received from the input sensor in a skin measurement mode.

According to an embodiment, a method for operating a display device includes: receiving sensing signals from an input sensor; sensing a touch area based on the sensing signals; outputting a compensation signal corresponding to capacitance compensation according to the touch area; extracting a representative value based on the compensation signal; outputting a moisture level signal based on the representative value; and causing, at least in part, an image corresponding to the moisture level signal to be displayed on a display panel.

According to an embodiment, a method for operating a display device includes: receiving sensing signals from an input sensor; extracting a representative value based on the sensing signals; sensing a touch area based on the sensing signals; outputting a compensation signal corresponding to capacitance compensation according to the touch area based on the representative value; outputting a moisture level signal based on the compensation signal; and causing, at least in part, an image corresponding to the moisture level signal to be displayed on a display panel.

The foregoing general description and the following detailed description are illustrative and explanatory and are intended to provide further explanation of the claimed subject matter.

BRIEF DESCRIPTION OF THE DRAWINGS

The accompanying drawings, which are included to provide a further understanding of the inventive concepts, and are incorporated in and constitute a part of this specification, illustrate embodiments of the inventive concepts, and, together with the description, serve to explain principles of the inventive concepts. In the drawings:

FIG. 10 is a view illustrating a portion of a digital sensing signal output from an analog-to-digital converter of FIG. 9 according to an embodiment;

FIG. 11 is a view illustrating a touch area determined based on valid data determined by an area compensator according to an embodiment;

DETAILED DESCRIPTION OF SOME EMBODIMENTS

Figure 1:
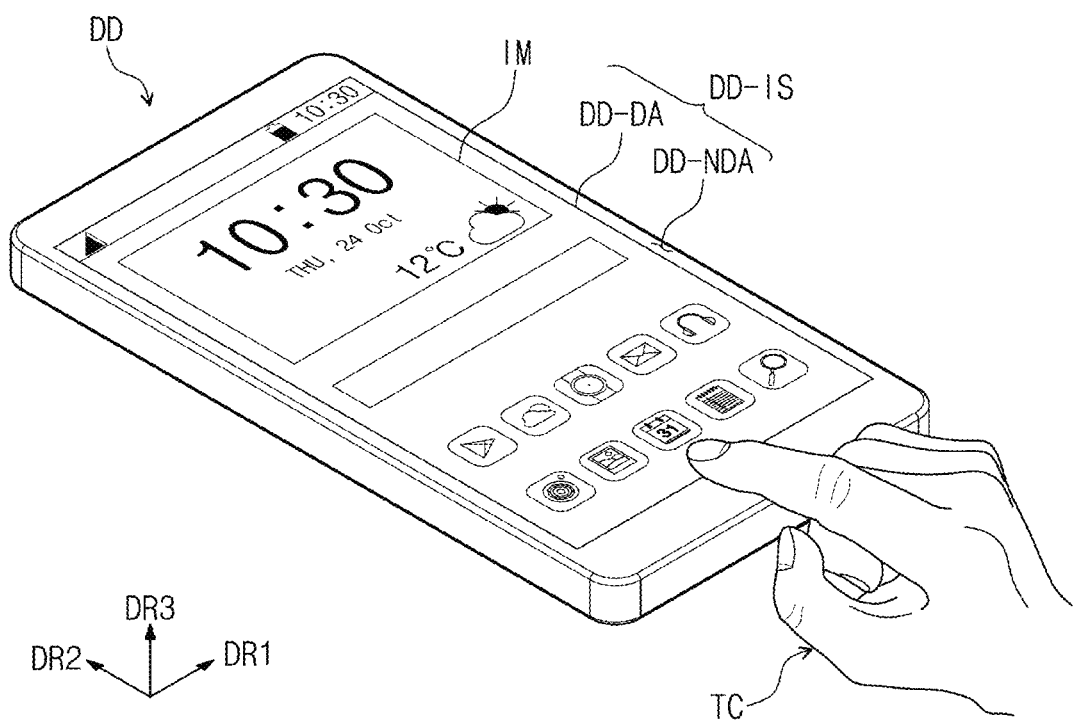
FIG. 1 is a perspective view of a display device according to an embodiment.

In the following description, for the purposes of explanation, numerous specific details are set forth in order to provide a thorough understanding of various embodiments. As used herein, the terms "embodiments" and "implementations" may be used interchangeably and are non-limiting examples employing one or more of the inventive concepts disclosed herein. It is apparent, however, that various embodiments may be practiced without these specific details or with one or more equivalent arrangements. In other instances, well-known structures and devices are shown in block diagram form to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing example features of varying detail of some embodiments. Therefore, unless otherwise specified, the features, components, modules, layers, films, panels, regions, aspects, etc. (hereinafter individually or collectively referred to as an "element" or "elements"), of the various illustrations may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. As such, the sizes and relative sizes of the respective elements are not necessarily limited to the sizes and relative sizes shown in the drawings. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element, it may be directly on, connected to, or coupled to the other element or intervening elements may be present. When, however, an element is referred to as being "directly on," "directly connected to," or "directly coupled to" another element, there are no intervening elements present. Other terms and/or phrases used to describe a relationship between elements should be interpreted in a like fashion, e.g., "between" versus "directly between," "adjacent" versus "directly adjacent," "on" versus "directly on," etc. Further, the term "connected" may refer to physical, electrical, and/or fluid connection. In addition, the DR1-axis, the DR2-axis, and the DR3-axis are not limited to three axes of a rectangular coordinate system, and may be interpreted in a broader sense. For example, the DR1-axis, the DR2-axis, and the DR3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one element's relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein should be interpreted accordingly.

The terminology used herein is for the purpose of describing some embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional views, isometric views, perspective views, plan views, and/or exploded illustrations that are schematic illustrations of idealized embodiments and/or intermediate structures. As such, variations from the shapes of the illustrations as a result of, for example, manufacturing techniques and/or tolerances, are to be expected. Thus, embodiments disclosed herein should not be construed as limited to the particular illustrated shapes of regions, but are to include deviations in shapes that result from, for instance, manufacturing. To this end, regions illustrated in the drawings may be schematic in nature and shapes of these regions may not reflect the actual shapes of regions of a device, and, as such, are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning consistent with their meaning in the context of the relevant art and will not be interpreted in an idealized or overly formal sense, unless expressly so defined herein.

As customary in the field, some embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some embodiments may be physically separated into two or more interacting and discrete blocks, units, and/or modules without departing from the inventive concepts. Further, the blocks, units, and/or modules of some embodiments may be physically combined into more complex blocks, units, and/or modules without departing from the inventive concepts.

Hereinafter, various embodiments will be explained in detail with reference to the accompanying drawings.

FIG. 1 is a perspective view of a display device DD according to an embodiment.

Referring to FIG. 1, the display device DD may display an image IM through a display surface DD-IS. The display surface DD-IS is parallel to a surface defined by a first directional axis DR1 and a second directional axis DR2. A normal direction of the display surface DD-IS, e.g., a thickness direction of the display device DD, is indicated as a third directional axis DR3.

A front surface (or a top surface) and a rear surface (or a bottom surface) of each of components or members, which will be described below, are distinguished by the third directional axis DR3. However, the first to third directional axes DR1, DR2, and DR3 as illustrated in the figures may be merely examples. Hereinafter, first to third directions may be directions indicated by the first to third directional axes DR1, DR2, and DR3 and designated by the same reference numerals, respectively.

Although the display device DD having a planar display surface DD-IS is illustrated as an embodiment, embodiments are not limited thereto. The display device DD may further include a curved display surface or any other suitable display surface. The display device DD may include a solid display surface. The solid display surface may include a plurality of display areas that indicate different directions. For example, the solid display surface may include a polygonal column-type display surface.

The display device DD according to some embodiments may be a rigid display device, but embodiments are not limited thereto. In an embodiment, the display device DD may be a flexible display device or a combination of a rigid and flexible display device. The flexible display device may include a foldable display device, a bendable display device of which a portion is bent, a slidable display device, and/or the like.

According to some embodiments, the display device DD may be capable of being applied to a mobile terminal and is illustrated as an example in FIG. 1. Although not shown, electronic modules, a camera module, a power module, and/or the like, which are mounted on a main board, may be disposed on a bracket/case together with the display device DD to constitute the mobile terminal. The display device DD according to some embodiments may be applied to large-sized electronic apparatuses, such as televisions and monitors, and small and middle-sized electronic apparatuses, such as tablet personal computer (PC), navigation units for vehicles, game consoles, smart watches, etc.

As illustrated in FIG. 1, the display surface DD-IS includes an image area DD-DA on which an image IM is displayed and a bezel area DD-NDA adjacent to the image area DD-DA. The bezel area DD-NDA may be an area on which an image is not displayed. FIG. 1 illustrates clock and icon images as examples of the image IM.

As illustrated in FIG. 1, the image area DD-DA may have a substantially rectangular shape. The "substantially rectangular shape" includes not only a rectangular shape as a mathematical sense but also a rectangular shape in which a vertex is not defined in a vertex area (or a corner area) but a boundary of a curve is defined.

The bezel area DD-NDA may surround the image area DD-DA. However, the embodiment is not limited thereto. In an embodiment, the image area DD-DA and the bezel area DD-NDA may be designed in different shapes. The bezel area DD-NDA may be disposed on only one side of the image area DD-DA. The bezel area DD-NDA may not be exposed to the outside according to coupled configurations of the display device DD and other components of an electronic apparatus (not shown).

The display device DD according to an embodiment may sense a user's input TC applied from the outside. The user's input TC may be one of various external inputs such as a portion of the user's body, a device such as a stylus pen, or a combination thereof. The display device DD may sense a user's input TC by sensing a change in one of reflected light, a temperature, a pressure, ultrasonic waves, and electromagnetic waves generated by the user's input TC, or a combination thereof. In this embodiment, it is assumed that the user's input TC is a touch input by a user's hand, which is applied to the front surface, but this is merely an example, and thus, as described above, the user's input TC may be provided in various forms. Also, the display device DD may sense the user's input TC applied to a side surface or a rear surface of the display device DD according to the structure of the display device DD, but is not limited to a specific embodiment.

Figure 2:
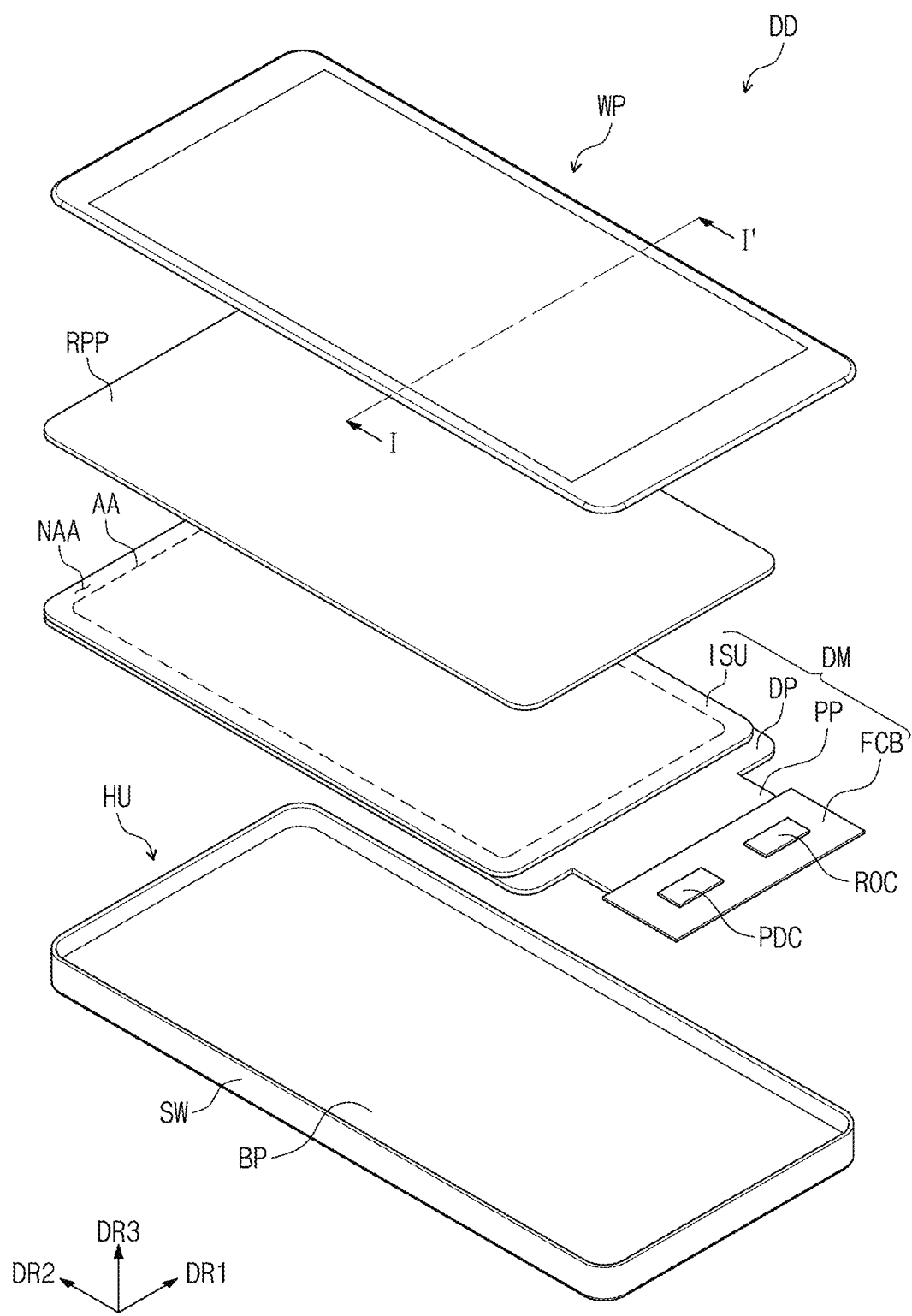
FIG. 2 is an exploded perspective view of the display device of FIG. 1 according to an embodiment.

FIG. 2 is an exploded perspective view of the display device DD according to an embodiment.

Referring to FIG. 2, the display device DD may include a window panel WP, an anti-reflection panel RPP, a display module DM, and a housing HU. As illustrated in FIGS. 1 and 2, the window panel WP and the housing HU are coupled to each other to define an appearance of the display device DD.

The window panel WP protects a top surface of the display panel DP. The window panel WP may include an optically transparent insulating material. For example, the window panel WP may include glass or plastic. The window panel WP may have a single-layered structure or a multi-layered structure. For example, the window panel WP may include a plurality of plastic films bonded to each other using an adhesive or include a glass substrate and a plastic film, which are bonded to each other using an adhesive.

The anti-reflection panel RPP may be disposed below the window panel WP. The anti-reflection panel RPP reduces reflectance of external light incident from an upper side of the window panel WP. In an embodiment, the anti-reflection panel RPP may be omitted or may be embedded in the display module DM.

The display module DM may display the image IM and sense an external input. The display module DM may include a display panel DP, an input sensor ISU, and a printed circuit board FCB.

An active area AA and a peripheral area NAA, which respectively correspond to the image area DD-DA and the bezel area DD-NDA of FIG. 1 may be defined on the display panel DP. The display panel DP may be a constituent that substantially generates the image IM. The image IM generated by the active area AA of the display panel DP is visually recognized by the user from the outside through the window panel WP.

The input sensor ISU senses an external input applied from the outside. As described above, the input sensor ISU may sense the external input provided to the window panel WP.

The display panel DP may include a pad area PP. A plurality of signal pads DP-PD and IS-PD (refer to FIG. 5) may be disposed in the pad area PP of the display panel DP. The display panel DP may be electrically connected to the printed circuit board FCB through the pads, such as the signal pads DP-PD and IS-PD. In an embodiment, a driving chip that generates signals for an operation of the display panel DP may be mounted in the pad area PP, but embodiments are not limited thereto.

The printed circuit board FCB may include various driving circuits for driving the display panel DP and the input sensor ISU or a connector for supplying power. In an embodiment, the printed circuit board FCB may include a panel driving circuit PDC for driving the display panel DP and a readout circuit ROC for driving the input sensor ISU. Each of the panel driving circuit PDC and the readout circuit ROC may be provided as an integrated circuit and mounted on the printed circuit board FCB. In another embodiment, the panel driving circuit PDC and the readout circuit ROC may be provided as one integrated circuit.

The housing HU includes a bottom part BP and a sidewall SW. The sidewall SW may extend from the bottom part BP. The housing HU may accommodate the display panel DP in an accommodation space defined by the bottom part BP and the sidewall SW. The window panel WP may be coupled to the sidewall SW of the housing HU. The sidewall SW of the housing HU may support an edge of the window panel WP.

The housing HU may include a material having relatively high rigidity. For example, the housing HU may include glass, plastic, or a metal or may include a plurality of frames and/or plates made of a combination of glass, plastic, and/or a metal. The housing HU may stably protect constituents of the display device DD accommodated in the internal space from external impact.

Figure 3:
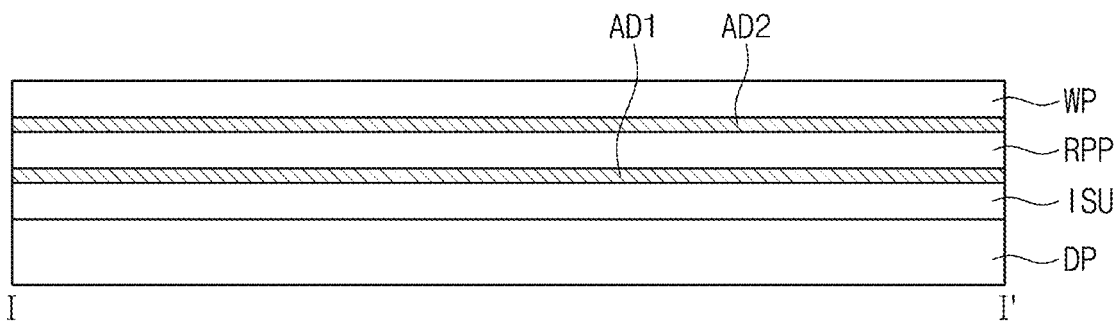
FIG. 3 is a cross-sectional view taken along sectional line I-I' of FIG. 2 according to an embodiment.
Figure 3:
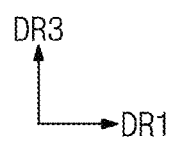

FIG. 3 is a cross-sectional view taken along sectional line I-I' of FIG. 2 according to an embodiment. It is noted that FIG. 3 illustrates a cross-section defined by the first directional axis DR1 and the third directional axis DR3. In FIG. 3, the components of the display device DD are simply illustrated to explain their lamination relationship.

The display device DD according to an embodiment may include a display panel DP, an input sensor ISU, an anti-reflection panel RPP, and a window panel WP. The components of at least some of the display panel DP, the input sensor ISU, the anti-reflection panel RPP, and the window panel WP may be formed through a continuous process, or at least some components may be coupled to each other through an adhesive member. In an embodiment, the input sensor ISU and the anti-reflection panel RPP may be coupled to each other by an adhesive member AD1. The anti-reflection panel RPP and the window panel WP may be coupled to each other by an adhesive member AD2.

Each of the adhesive members AD1 and AD2 may be a transparent adhesive member, such as a pressure sensitive adhesive film (PSA), an optically clear adhesive film (OCA), or an optically clear resin (OCR). The adhesive member(s) described below may include a conventional adhesive or an adhesive agent. In an embodiment, the anti-reflection panel RPP and the window panel WP may be replaced by other components or omitted.

In FIG. 3, the input sensor ISU is formed together with the display panel DP among the input sensor ISU, the anti-reflection panel RPP, and the window panel WP through a continuous process and is directly disposed on the display panel DP. For the purposes of this disclosure, "a component B is disposed directly on a component A" means that no separate adhesive layer/adhesive member is disposed between the component A and the component B. The component B is formed through a continuous process on a base surface provided by the component A after the component A is formed.

According to an embodiment, each of the anti-reflection panel RPP and the window panel WP is provided in a "panel" type, and the input sensor ISU is provided in a "layer" type. The "panel" type includes a base layer that provides a base surface, for example, a synthetic resin film, a composite film, a glass substrate, and/or the like, but the base layer may be omitted in the "layer" type. For instance, the "layer" type components are disposed on the base surface provided by the other component. In an embodiment, at least one of the anti-reflection panel RPP and the window panel WP may be provided in the "layer" type.

The display panel DP generates an image IM, and the input sensor ISU acquires coordinate information of an external input (e.g., a touch event). In some embodiments, the display device DD may further include a protective member disposed on a bottom surface (or a rear surface) of the display panel DP. The protective member and the display panel DP may be coupled to each other through an adhesive member.

The display panel DP according to an embodiment may be an emission type display panel, but is not limited thereto. For example, the display panel DP may be an organic light emitting display panel or a quantum dot light emitting display panel. The panels are classified according to the material of the light emitting element. An emission layer of the organic light emitting display panel may include an organic light emitting material. An emission layer of the quantum dot light emitting display panel may include a quantum dot and/or a quantum rod. Hereinafter, the display panel DP will be described as an organic light emitting display panel.

The anti-reflection panel RPP reduces reflectance of external light incident from an upper side of the window panel WP. The anti-reflection panel RPP according to an embodiment may include at least one of a phase retarder and a polarizer. The phase retarder may be provided in a film type or a liquid crystal coating type. The polarizer may also be provided in a film type or liquid crystal coating type. The film type may include an elongation-type synthetic resin, and the liquid crystal coating type may include liquid crystals that are arranged in a predetermined arrangement. Each of the phase retarder and the polarizer may further include a protection film. The phase retarder and polarizer itself or the protection film may be defined as the base layer of the anti-reflection panel RPP.

The anti-reflection panel RPP according to an embodiment may include color filters. The color filters have a predetermined arrangement. The arrangement of the color filters may be determined in consideration of emission colors of pixels provided in the display panel DP. The anti-reflection panel RPP may further include a black matrix adjacent to the color filters.

The anti-reflection panel RPP according to an embodiment may include a destructive interference structure. For example, the destructive interference structure may include a first reflective layer and a second reflective layer, which are disposed on layers different from each other. First reflected light and second reflected light, which are respectively reflected by the first reflection layer and the second reflection layer, may destructively interfere with each other to reduce the reflectance of the external light.

The window panel WP according to an embodiment may include a glass substrate and/or a synthetic resin film. The window panel WP is not limited to a single layer. The window panel WP may include two or more layers or films bonded to each other by an adhesive member. The window panel WP may further include a functional coating layer. The functional coating layer may include at least one of an anti-fingerprint layer, an anti-reflection layer, a hard coating layer, and the like.

The input sensor ISU and the display panel DP will now be described in more detail below.

Figure 4:
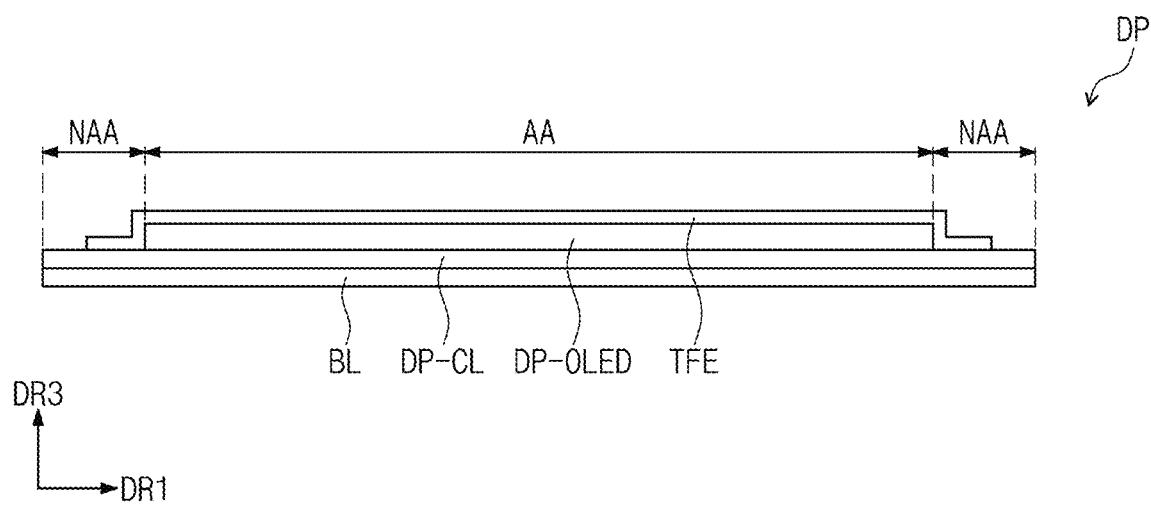
FIG. 4 is a cross-sectional view of a display panel of FIG. 3 according to an embodiment.
Figure 4:
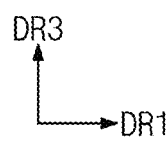

FIG. 4 is a cross-sectional view of the display panel DP of FIG. 3 according to an embodiment.

As illustrated in FIG. 4, the display panel DP may include a base layer BL, a circuit element layer DP-CL disposed on the base layer BL, a light emitting element layer DP-OLED, and a thin film encapsulation layer TFE. An active area AA and a peripheral area NAA, which respectively correspond to the image area DD-DA and the bezel area DD-NDA of FIG. 1, may be defined on the display panel DP. In this specification, that "an area/portion and another area/portion correspond to each other" means "overlapping with each other," but is not limited to having the same area and/or the same shape.

The base layer BL may include at least one synthetic resin film. The base layer BL may include at least one of a glass substrate, a metal substrate, and an organic/inorganic composite substrate.

A circuit element layer DP-CL is disposed on the base layer BL. The circuit element layer DP-CL includes at least one insulating layer and circuit elements. The insulating layer includes at least one inorganic layer and at least one organic layer. The circuit elements may include signal lines, a pixel driving circuit, and the like.

The light emitting element layer DP-OLED is disposed on the circuit element layer DP-CL. The light emitting element layer DP-OLED may include at least organic light emitting diodes as light emitting elements. The light emitting element layer DP-OLED may further include an organic layer, such as a pixel defining layer.

The thin film encapsulation layer TFE may be disposed on the light emitting element layer DP-OLED to encapsulate the light emitting element layer DP-OLED. The thin film encapsulation layer TFE may entirely cover the active area AA. The thin film encapsulation layer TFE may cover a partial area of the peripheral area NAA.

The thin film encapsulation layer TFE include a plurality of thin films. One portion of the thin films may be disposed to improve optical efficiency, and the portion of the thin film may be disposed to protect the organic light emitting diodes.

Figure 5:
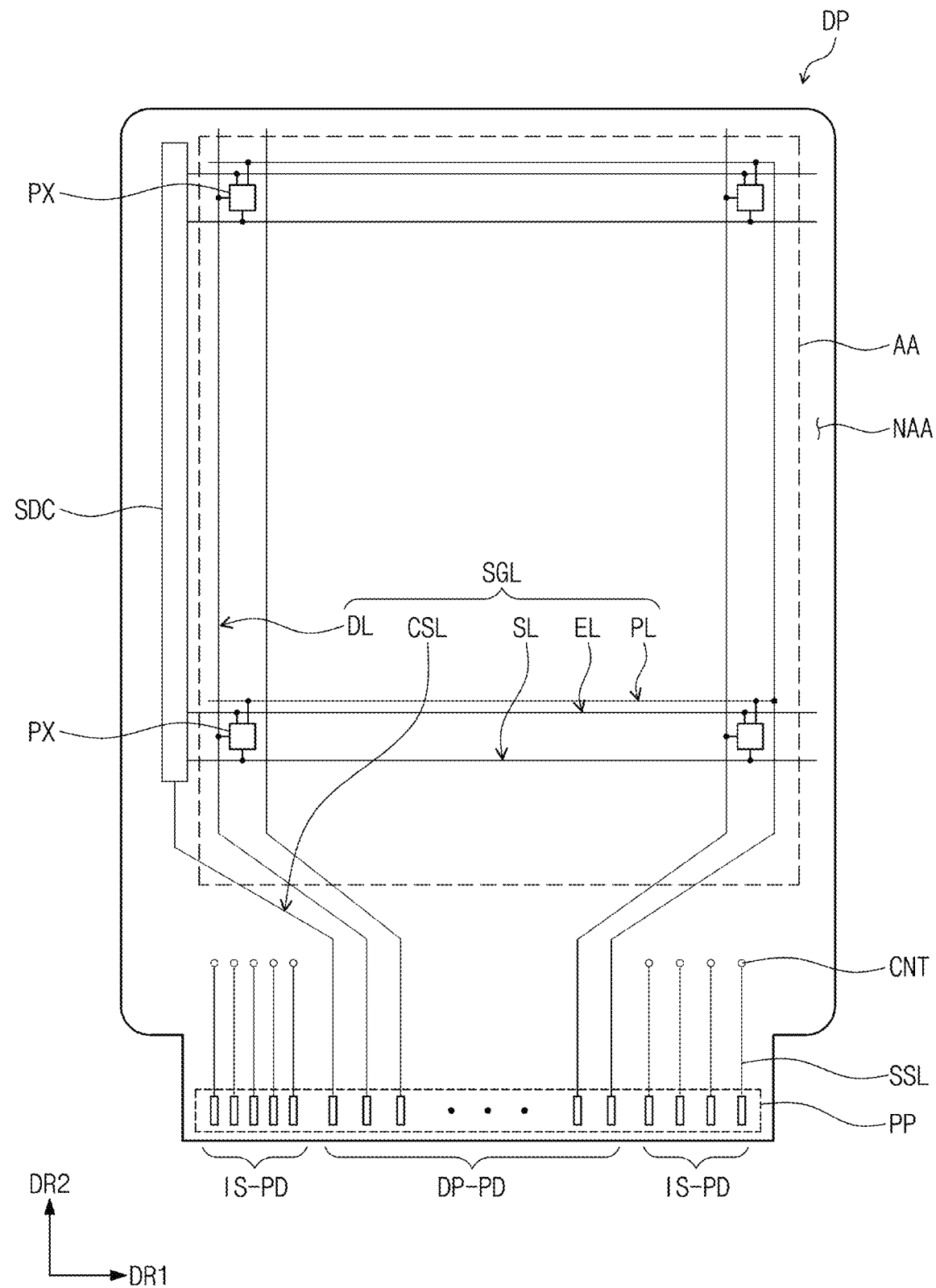
FIG. 5 is a plan view of a display panel according to an embodiment.

FIG. 5 is a plan view of the display panel DP according to an embodiment.

As illustrated in FIG. 5, the display panel DP includes a scan driving circuit SDC, a plurality of signal lines SGL (hereinafter, referred to as signal lines), a plurality of signal pads DP-PD and IS-PD (hereinafter, referred to as signal pads), and a plurality of pixels PX (hereinafter, referred to as pixels).

The scan driving circuit SDC generates a plurality of scan signals (hereinafter, referred to as scan signals) to sequentially output the scan signals to a plurality of scan lines SL (hereinafter, referred to as scan lines) that will be described later. The scan driving circuit SDC may output not only the scan signals, but also other control signals to the pixels PX.

The scan driving circuit SDC may include a plurality of transistors formed through a same process as the process of forming the transistors in the pixels PX.

The signal lines SGL include scan lines SL, data lines DL, a power line PL, emission control lines EL, and a control signal line CSL. Each of the scan lines SL, the data lines DL, and the emission control lines EL is connected to a corresponding pixel PX among the pixels PX. The power line PL is commonly connected to the pixels PX. The control signal line CSL may provide control signals to the scan driving circuit SDC. The power line PL may provide a voltage for an operation of the pixels PX. The power line PL may include a plurality of lines that provide different voltages.

In an embodiment, the signal lines SGL may further include auxiliary lines SSL. The auxiliary lines SSL are signal lines connected to the input sensor ISU (refer to FIG. 2). In an embodiment, the auxiliary lines SSL may be omitted. The auxiliary lines SSL are connected to contact holes CNT, respectively. The auxiliary lines SSL may be electrically connected to signal lines of an input sensor ISU (refer to FIG. 6) described later through contact holes CNT.

The signal pads DP-PD and IS-PD may include first type signal pads DP-PD connected to the data lines DL, the power line PL, and the control signal line CSL and second type signal pads IS-PD connected to the auxiliary lines SSL. The first type signal pads DP-PD and the second type signal pads IS-PD are disposed adjacent to each other in a pad area PP defined in a portion of the peripheral area NAA. The signal pads DP-PD and IS-PD may be formed through the same process without distinguishing laminated structures or forming materials from each other.

The active area AA may be defined as an area on which the pixels PX are disposed. A plurality of electronic elements may be disposed in the active area AA. The electronic elements include an organic light emitting diode provided in each of the pixels PX and a pixel driving circuit connected to the organic light emitting diode. The scan driving circuit SDC, the signal lines SGL, the signal pads DP-PD and IS-PD, and the pixel driving circuit may be provided in the circuit element layer DP-CL illustrated in FIG. 4.

Although not shown in the drawings, each of the pixels PX may include a plurality of transistors, a capacitor, and an organic light emitting diode. The pixels PX emit light in response to signals received through the scan lines SL, the data lines DL, the emission control lines EL, and the power line PL.

The signal pads DP-PD and IS-PD of the display panel DP may be electrically connected to the printed circuit board FCB illustrated in FIG. 2.

A portion of the display panel DP illustrated in FIG. 4 may be bent. A portion of the peripheral area NAA of the display panel DP may be bent. For instance, a portion of the peripheral area NAA may be bent based on a bending axis parallel to, for example, the first direction DR1. The bending axis may be defined to overlap a portion of the data lines DL and a portion of the auxiliary lines SSL.

Figure 6:
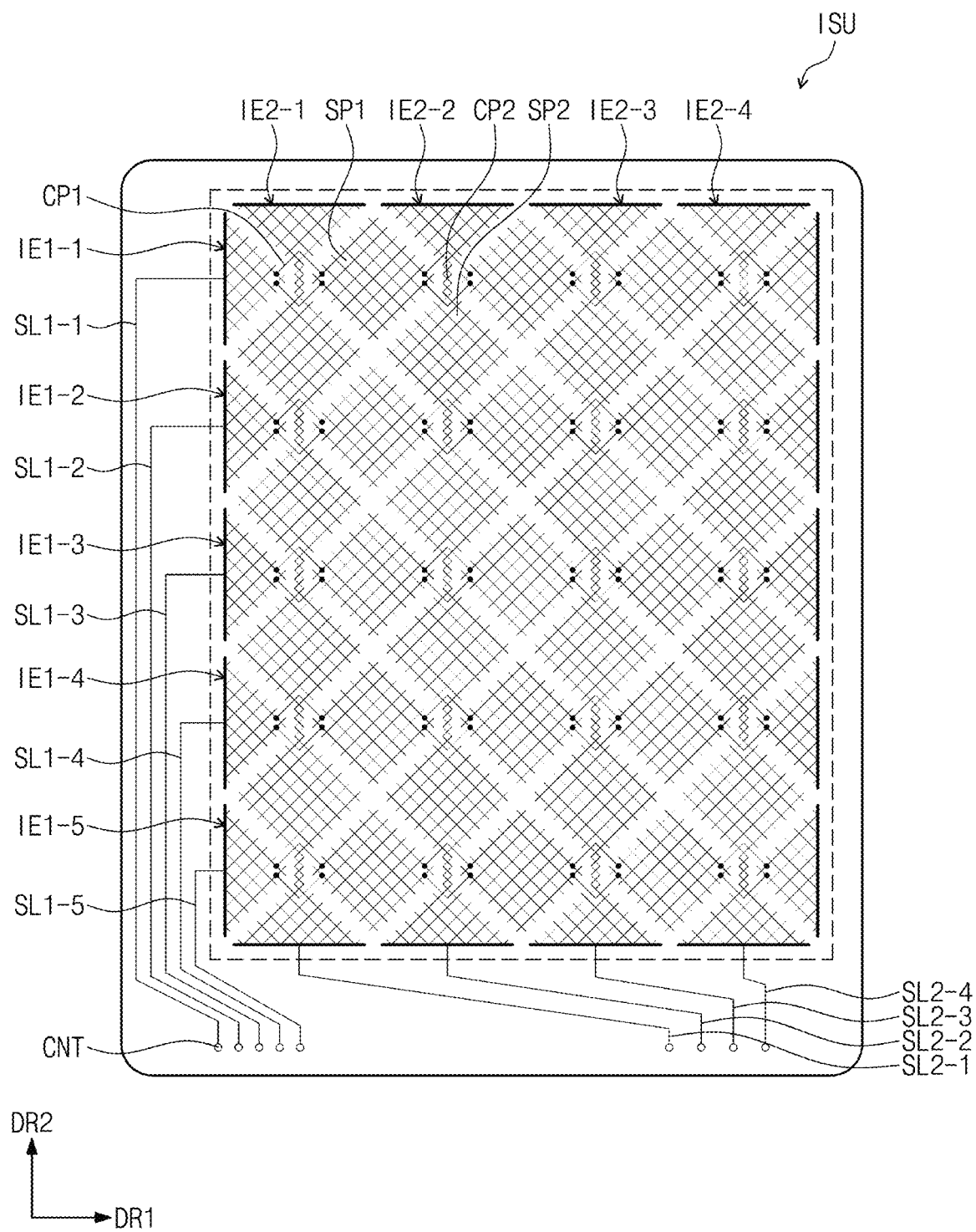
FIG. 6 is a plan view illustrating constituents of an input sensor according to an embodiment.

FIG. 6 is a plan view of the input sensor ISU according to an embodiment.

Referring to FIG. 6, the input sensor ISU according to an embodiment may include first sensing electrodes IE1-1 to IE1-5, first signal lines SL1-1 to SL1-5 connected to the first sensing electrodes IE1-1 to IE1-5, second sensing electrodes IE2-1 to IE2-4, and second signal lines SL2-1 to SL2-4 connected to the second sensing electrodes IE2-1 to IE2-4.

The first sensing electrodes IE1-1 to IE1-5 and the second sensing electrodes IE2-1 to IE2-4 cross each other. The first sensing electrodes IE1-1 to IE1-5 are arranged in the second direction DR2, and each of the first sensing electrodes IE1-1 to IE1-5 extends in the first direction DR1. The second sensing electrodes IE2-1 to IE2-4 are arranged in the first direction DR1, and each of the second sensing electrodes IE2-1 to IE2-4 extends in the second direction DR2.

Each of the first sensing electrodes IE1-1 to IE1-5 includes first sensing patterns SP1 and first connection patterns CP1, which are disposed in the active area AA. Each of the second sensing electrodes IE2-1 to IE2-4 includes second sensing patterns SP2 and second connection patterns CP2, which are disposed in the active area AA. Each of two first sensing patterns disposed at both ends of the input sensor ISU among the first sensing patterns SP1 may have a smaller size, for example, have a size corresponding to about ½ the size of the first sensing pattern disposed at a central area of the input sensor ISU. Each of two second sensing patterns disposed at both ends of the input sensor ISU among the second sensing patterns SP2 may have a smaller size, for example, have a size corresponding to about ½ the size of the second sensing pattern disposed at a central area of the input sensor ISU.

In each of the first sensing electrodes IE1-1 to IE1-5, the first sensing patterns SP1 are arranged along the first direction DR1, and in each of the second sensing electrodes IE2-1 to IE2-4, the second sensing patterns SP2 are arranged along the second direction DR2. Each of the first connection patterns CP1 connects adjacent first sensing patterns SP1 to each other, and each of the second connection patterns CP2 connects adjacent second sensing patterns SP2 to each other.

In FIG. 6, four second sensing patterns SP2 are disposed in the first direction DR1, and five first sensing patterns SP1 are disposed in the second direction DR1. However, embodiments are not limited thereto. In an embodiment, the number of first sensing patterns SP1 and the number of second sensing patterns SP2 may be variously changed.

The first signal lines SL1-1 to SL1-5 are connected to an end of the first sensing electrodes IE1-1 to IE1-5, respectively. The second signal lines SL2-1 to SL2-4 are connected to an end of the second sensing electrodes IE2-1 to IE2-4. In an embodiment, the first signal lines SL1-1 to SL1-5 may be connected to both ends of the first sensing electrodes IE1-1 to IE1-5, respectively. Also, the second signal lines SL2-1 to SL2-4 may be connected to both ends of the second sensing electrodes IE2-1 to IE2-4, respectively. The first signal lines SL1-1 to SL1-5 and the second signal lines SL2-1 to SL2-4 may be disposed in the peripheral area NAA.

The first signal lines SL1-1 to SL1-5 and the second signal lines SL2-1 to SL2-4 are electrically connected to the auxiliary lines SSL illustrated in FIG. 5 through the contact holes CNT.

Each of the first sensing electrodes IE1-1 to IE1-5 and the second sensing electrodes IE2-1 to IE2-4 may have a mesh shape. However, the shape of the first sensing electrodes IE1-1 to IE1-5 and the second sensing electrodes IE2-1 to IE2-4 is not limited thereto, and thus, may be variously changed.

The first sensing electrodes IE1-1 to IE1-5 and the second sensing electrodes IE2-1 to IE2-4 may not overlap an emission layer EML (refer to FIG. 7), and thus, may not be visually recognized by the user.

Each of the first sensing electrodes IE1-1 to IE1-5 and the second sensing electrodes IE2-1 to IE2-4 having the mesh shape may include at least one of silver, aluminum, copper, chromium, nickel, and titanium, which are capable of being processed at a low temperature, but is not limited thereto.

Figure 7:
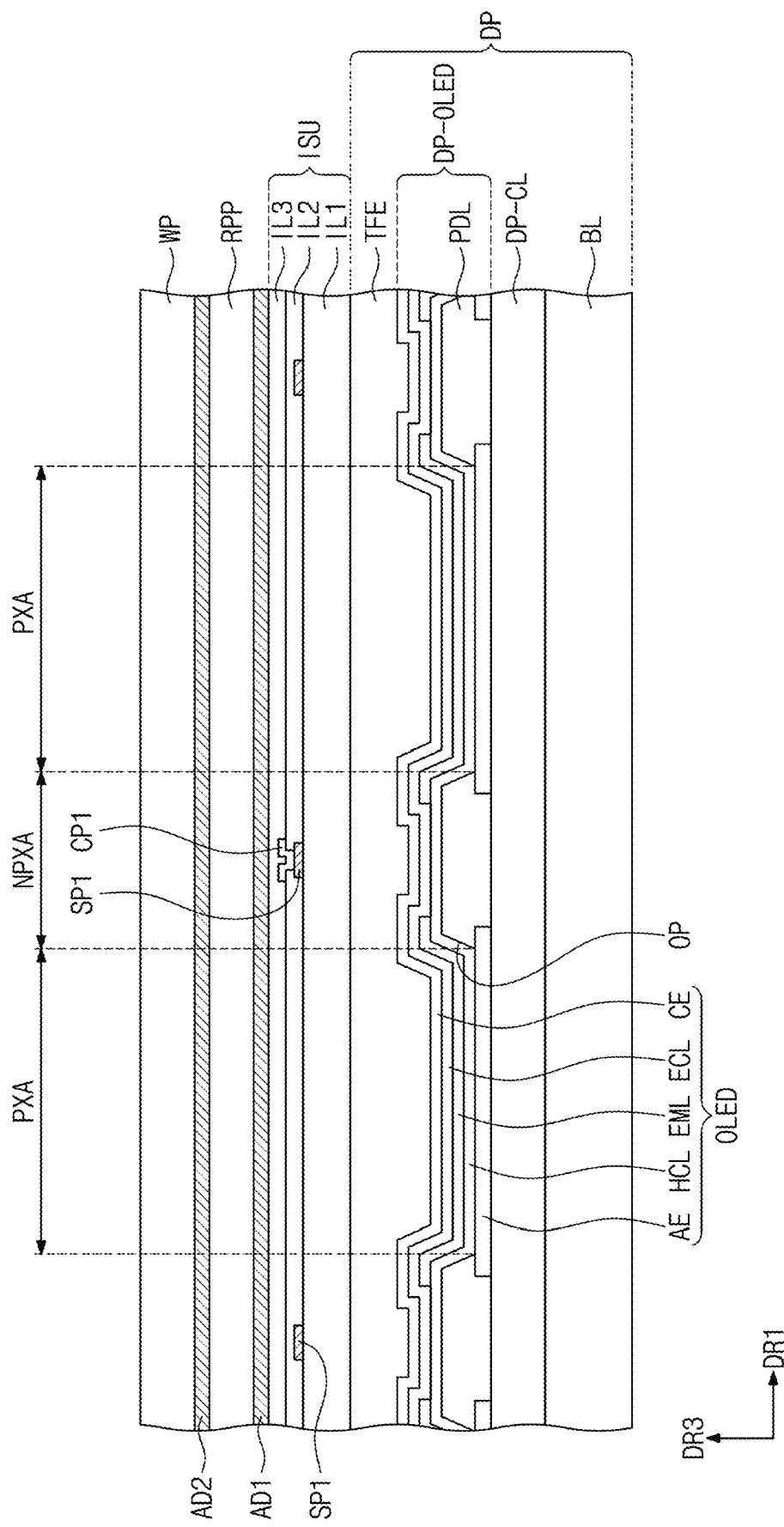
FIG. 7 is a cross-sectional view of a display device according to an embodiment.

FIG. 7 is a cross-sectional view of the display device according to an embodiment.

As illustrated in FIG. 7, the display panel DP may include a base layer BL, a circuit element layer DP-CL disposed on the base layer BL, a light emitting element layer DP-OLED, and a thin film encapsulation layer TFE. In some embodiments, the display panel DP may further include functional layers, such as the anti-reflection layer, a reflective index adjustment layer, and/or the like.

The base layer BL may include a synthetic resin film. A synthetic resin layer may be disposed on a working substrate used for manufacturing the display panel DP. Thereafter, a conductive layer, an insulating layer, and the like may be disposed on the synthetic resin layer. When the working substrate is removed, the synthetic resin layer corresponds to the base layer BL. The synthetic resin layer may be a polyimide resin layer, and the material thereof is not particularly limited. In addition, the base layer BL may include at least one of glass substrate, a metal substrate, and an organic/inorganic composite substrate.

The circuit element layer DP-CL includes at least one insulating layer and a circuit element. Hereinafter, the insulating layer provided in the circuit element layer DP-CL may be referred to as an intermediate insulating layer. The intermediate insulation layer includes at least one intermediate inorganic film and at least one intermediate organic film. The circuit element includes the signal line and the driving circuit of the pixel. The circuit element layer DP-CL may be formed through a process of forming an insulating layer, a semiconductor layer, and a conductive layer by coating or deposition and a process of patterning the insulating layer, the semiconductor layer, and the conductive layer by a photolithography process.

The light emitting element layer DP-OLED may include a pixel defining layer PDL and an organic light emitting diode OLED. The pixel defining layer PDL may include an organic material. A first electrode AE is disposed on the circuit element layer DP-CL. The pixel defining layer PDL is disposed on the first electrode AE. An opening OP is defined in the pixel defining layer PDL. The opening OP of the pixel defining layer PDL exposes at least a portion of the first electrode AE. In an embodiment, the pixel defining layer PDL may be omitted.

A hole control layer HCL may be disposed on the first electrode AE. An emission layer EML is disposed on the hole control layer HCL. The emission layer EML may be disposed in an area corresponding to the opening OP. For instance, the emission layer EML may be provided to be separated from each other in each of the pixels PX (refer to FIG. 5). Also, the emission layer EML may include an organic material and/or an inorganic material. The emission layer EML may generate light having a predetermined color.

An electron control layer ECL is disposed on the emission layer EML. A second electrode CE is disposed on the electron control layer ECL. The second electrode CE may be commonly disposed in (or with respect to) the pixels PX.

The thin film encapsulation layer TFE is disposed on the second electrode CE. The thin film encapsulation layer TFE seals the light emitting element layer DP-OLED. The thin film encapsulation layer TFE includes at least one insulating layer. The thin film encapsulation layer TFE according to an embodiment may include at least one inorganic film (hereinafter, referred to as an encapsulation inorganic film). The thin film encapsulation layer TFE according to an embodiment may include at least one organic film (hereinafter, referred to as an encapsulation organic film) and at least one encapsulation inorganic film.

The encapsulation inorganic film protects the light emitting element layer DP-OLED against moisture/oxygen, and the encapsulation organic film protects the light emitting element layer DP-OLED against foreign substances, such as dust particles. The encapsulation inorganic film may include at least one of a silicon nitride layer, a silicon oxy nitride layer, a silicon oxide layer, a titanium oxide layer, and an aluminum oxide layer, but is not limited thereto. The encapsulation organic film may include an acrylic-based organic layer, but is not limited thereto.

The input sensor ISU includes a base layer IL1, first and second conductive layers disposed on the base layer IL1, and first and second insulating layers IL2 and IL3 disposed on the base layer IL1. The base layer IL1 may include an inorganic material, for example, a silicon nitride layer. The inorganic film disposed at the uppermost side of the thin film encapsulation layer TFE may also include silicon nitride. The base layer IL1 and the silicon nitride layer of the thin film encapsulation layer TFE may be disposed under different deposition conditions.

The first conductive layer is disposed on the base layer IL1. The first conductive layer may include a first sensing pattern SP1, a second sensing pattern SP2, and a second connection pattern CP2 (refer to FIG. 6). The second conductive layer is disposed on the first conductive layer. The second conductive layer may include a first connection pattern CP1. The first insulating layer IL2 is disposed between the first conductive layer and the second conductive layer. The first insulating layer IL2 spaces and separates the first conductive layer from the second conductive layer on the cross-section. A contact hole for partially exposing the first sensing pattern SP1 may be provided in the first insulating layer IL2, and the first connection pattern CP1 may be connected to the first sensing pattern SP1 through the contact hole. The second insulating layer IL3 is disposed on the first insulating layer IL2. The second insulating layer IL3 may cover the second conductive layer. The second insulating layer IL3 protects the second conductive layer from the external environment.

The mesh lines of the first sensing pattern SP1 and the second sensing pattern SP2 may define a plurality of mesh holes. The mesh lines may have a three-layered structure of titanium/aluminum/titanium, but embodiments are not limited thereto.

In the display device DD, the input sensor ISU may be disposed directly on the display panel DP. The meaning of being disposed directly on means that an adhesive film is not disposed between the input sensor ISU and the display panel DP. For instance, the input sensor ISU may be formed on the display panel DP through a continuous process. In this case, the input sensor ISU may be expressed or otherwise referred to as an input sensing layer.

A portion on which the first electrode AE and the emission layer EML are disposed may be referred to as a pixel area PXA. The pixel areas PXA may be disposed to be spaced apart from each other in the first direction DR1 and the second direction DR2 (refer to FIG. 5). A non-pixel area NPAX may be disposed between the pixel areas PXA and may surround the pixel area PXA.

An anti-reflection panel RPP may be disposed on a top surface of the input sensor ISU. According to an embodiment, the anti-reflection panel RPP may include a polarizing film. The anti-reflection panel RPP may further include a protective film and/or other functional films in addition to the polarizing film, but hereinafter, only the polarizing film is illustrated for convenience of description. An adhesive member AD1 may be disposed between the anti-reflection panel RPP and the input sensor ISU. Thus, the anti-reflection panel RPP may be bonded to the input sensor ISU by the adhesive member AD1. The window panel WP may be bonded to the anti-reflection panel RPP through an adhesive member AD2.

Referring again to FIG. 6, the input sensor ISU may be a capacitive touch sensor. One of the first sensing electrodes IE1-1 to IE1-5 and the second sensing electrodes IE2-1 to IE2-4 receives a driving signal, and the other outputs a variation in capacitance between the first sensing electrodes IE1-1 to IE1-5 and the second sensing electrodes IE2-1 to IE2-4 as a sensing signal. In an embodiment, when the first sensing electrodes IE1-1 to IE1-5 receive a driving signal (or a transmission signal), the second sensing electrodes IE2-1 to IE2-4 may be capacitively coupled to the first sensing electrodes IE1-1 to IE1-4. When a portion of a user's body is disposed on (or near) a first sensing electrode IE1-4 among the first sensing electrodes IE1-1 to IE1-4, which are capacitively coupled to each other, capacitance between the first sensing electrode IE1-4 and a second sensing electrode IE2-1 among the second sensing electrodes IE2-1 to IE2-4 may be changed. The readout circuit ROC (refer to FIG. 2) may detect the changed capacitance of the sensing signal received from a second signal line SL2-1 among the second signal lines SL2-1 to SL2-4 connected to the second sensing electrode IE2-1 to calculate or determine coordinate information of the user's touch position. For example, the readout circuit ROC according to an embodiment may detect the changed capacitance of the sensing signal received from the second signal lines SL2-1 to SL2-4 to sense a user's skin conditions, for example, a skin moisture level (or skin hydration level).

Figure 8:
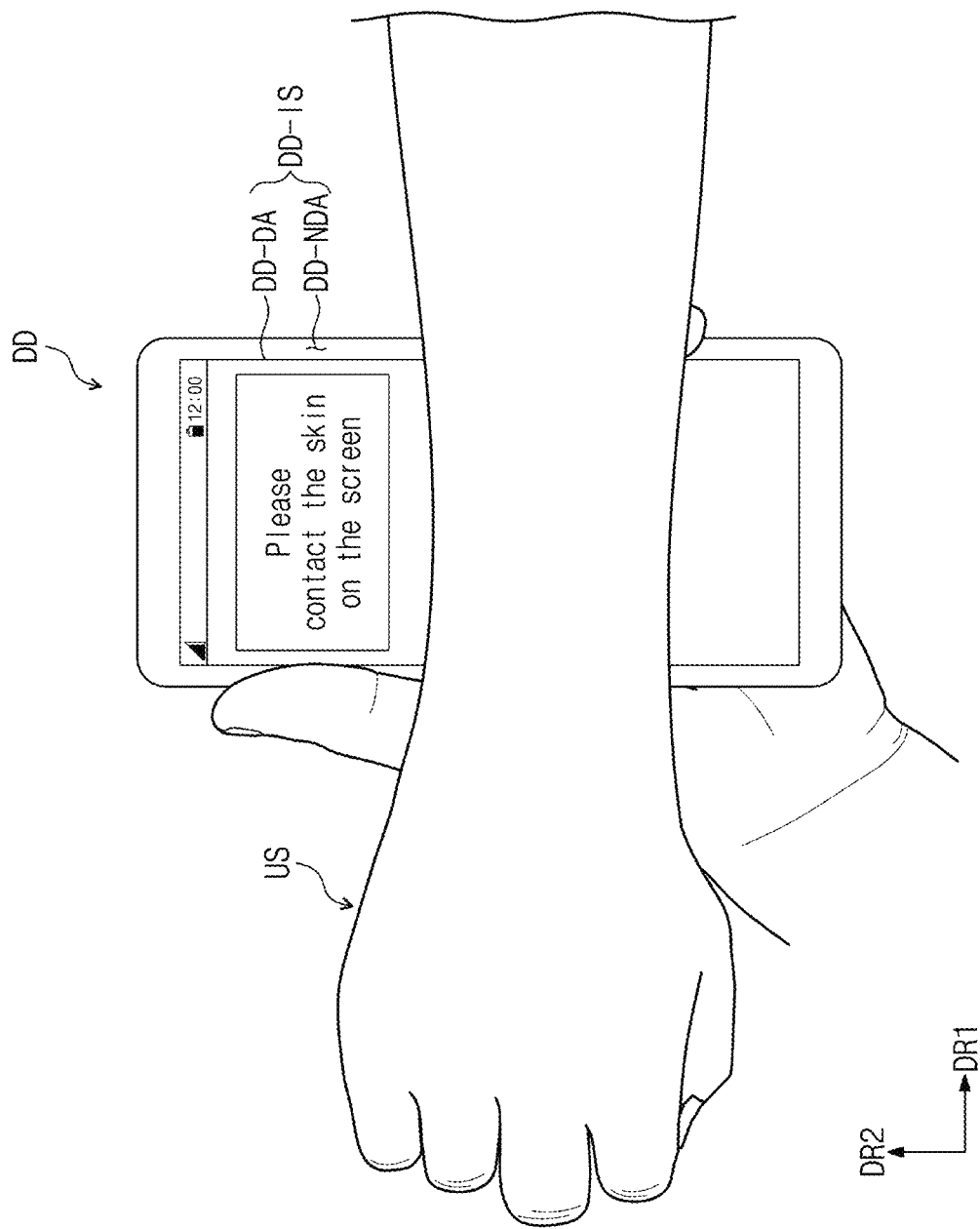
FIG. 8 is a view illustrating an example of measuring a skin condition using a display device according to an embodiment.

FIG. 8 is a view illustrating an example of measuring a skin condition using the display device DD according to an embodiment.

As illustrated in FIG. 8, in a skin measurement mode, the display device DD may display a message indicating a start of the skin measurement mode on an image area DD-DA of a display surface DD-IS. A user US checks the message while holding the display device DD with one hand and allows a skin of a portion of the body to be measured to be in contact with the image area DD-DA of the display device DD. In an embodiment, as illustrated in FIG. 8, the user US may allow a skin of an arm portion to be in contact with the image area DD-DA of the display device DD. Although FIG. 8 illustrates that the user US measuring the moisture level on an inner portion of a wrist of the arm, embodiments are not limited thereto. The position at which the user US wants to measure skin moisture levels may be various, such as a face, a leg, an abdomen, etc.

The display device DD may measure a moisture level of the skin of the portion of the user US that is in contact with the image area DD-DA and then display the result.

When the body's skin is in direct contact with the display surface DD-IS, a change in capacitance occurs due to a difference in permittivity between moisture and air in the skin. The display device DD may measure an amount of moisture in the skin by sensing a variation in capacitance.

Figure 9:
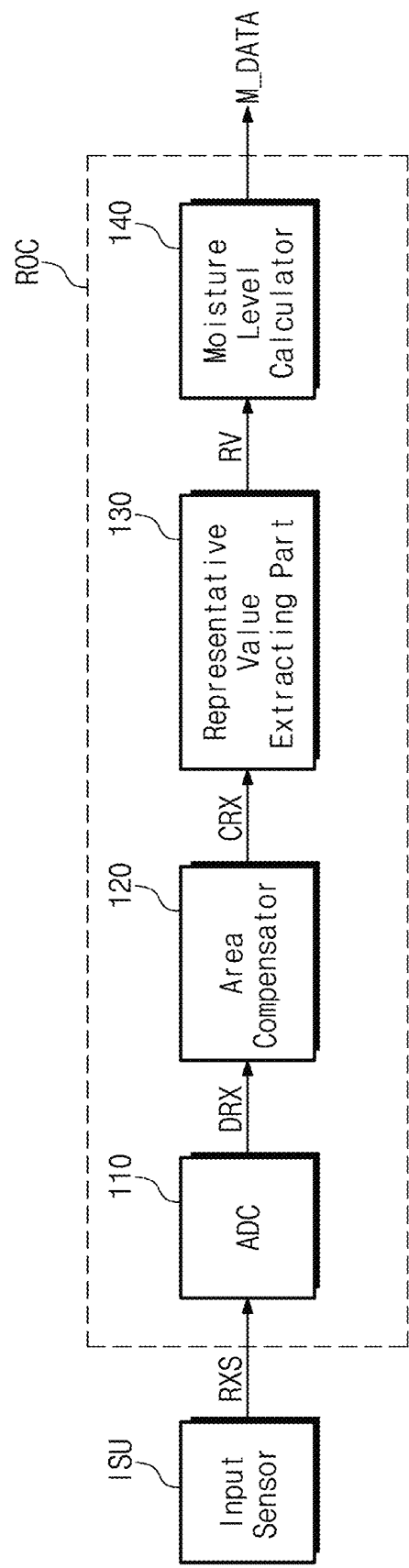
FIG. 9 is a block diagram illustrating a configuration of a readout circuit according to an embodiment.

FIG. 9 is a block diagram illustrating a configuration of the readout circuit ROC according to an embodiment.

Referring to FIG. 9, the readout circuit ROC may include an analog-to-digital converter 110, an area compensator 120, a representative value extracting part 130, and a moisture level calculator 140.

The analog-to-digital converter 110 may receive a sensing signal RXS from the input sensor ISU. The sensing signal RXS may be an analog capacitive signal associated with a touch of the user US (refer to FIG. 8). The analog-to-digital converter 110 converts the sensing signal RXS into a digital sensing signal DRX.

The area compensator 120 calculates (or determines) a touch area based on the digital sensing signal DRX and outputs a compensation signal CRX that performs capacitance compensation according to the touch area. The touch area may be a contact area between the user's body and the input sensor ISU.

Figure 10:
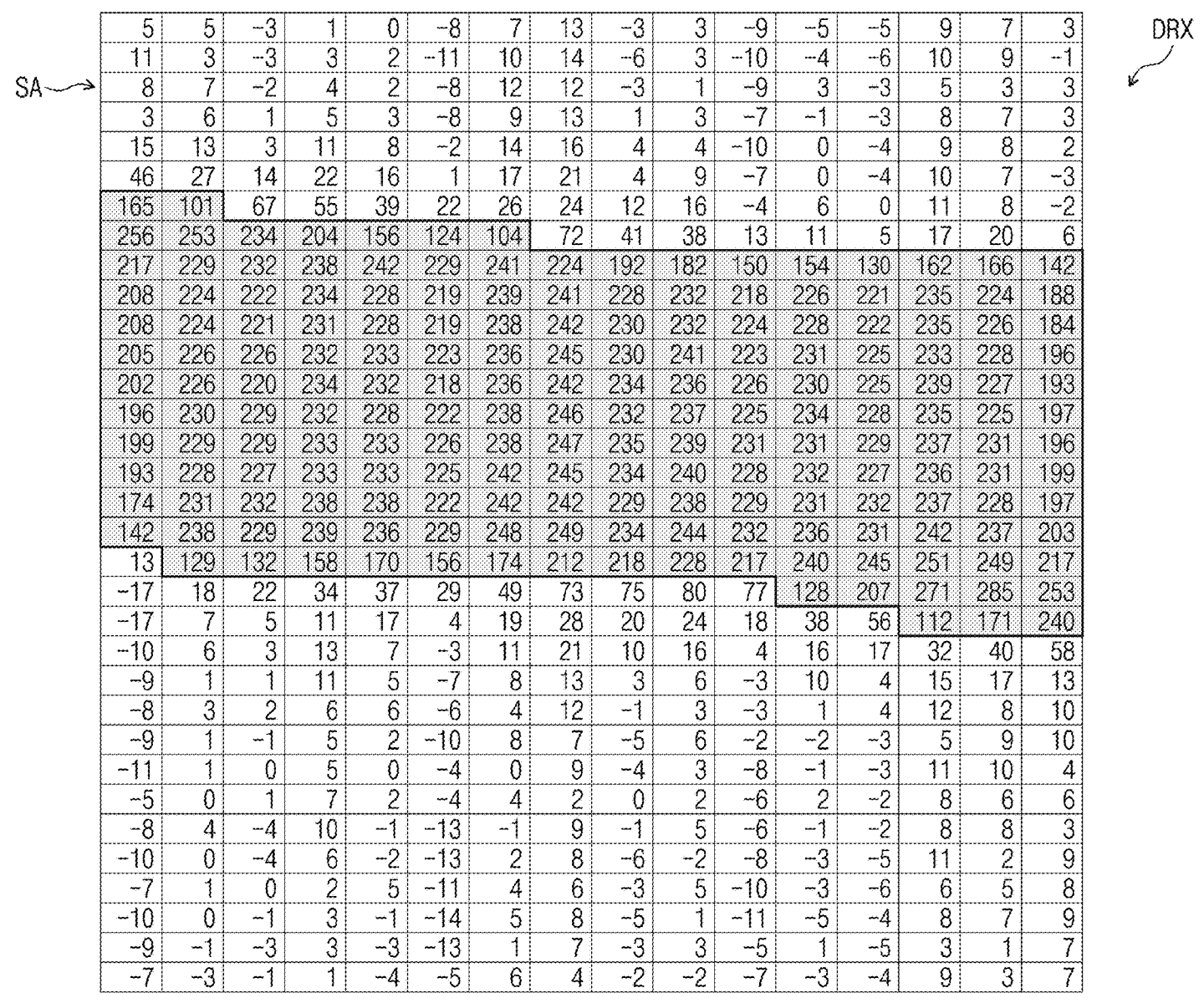

FIG. 10 is a view exemplarily illustrating a portion of the digital sensing signal DRX output from the analog-to-digital converter 110 illustrated in FIG. 9.

In FIG. 10, the figure indicates the digital sensing signal DRX which is the digital signal converted from the sensing signal RXS from the second sensing patterns SP2 of the second detection electrodes IE2-1 to IE2-4 of FIG. 6 by the analog-to-digital converter 110.

In an embodiment, a portion of the body of the user US, e.g., the arm, is in contact with a central portion of the display device DD in parallel to the first direction DR1. The digital sensing signal DRX may have various values according to a degree of contact between the arm of the user US and the input sensor ISU.

In an embodiment, the digital sensing signal DRX corresponding to the second sensing pattern in complete contact with the arm of the user US among the second sensing patterns SP2 (refer to FIG. 6) has a high value (for example, about 100 or more). The digital sensing signal DRX corresponding to the second sensing pattern in weakly contact with the arm of the user US among the second sensing patterns SP2 (refer to FIG. 6) has a middle value (for example, ranging of about 20 to about 100). The digital sensing signal DRX corresponding to the second sensing pattern not in contact with the arm of the user US among the second sensing patterns SP2 (refer to FIG. 6) has a low value (for example, about 20 or less).

The area compensator 120 classifies the digital sensing signal DRX having the middle value and the low value among the digital sensing signals DRX as noise and may regard only the digital sensing signal DRX having the high value (e.g., about 100 or more) as valid data. For example, the area compensator 120 may regard the digital sensing signal DRX having a value higher than a reference value (e.g., about 100 or more) among the digital sensing signals DRX as the valid data.

In an embodiment, the area compensator 120 may select the digital sensing signal DRX having a value greater than a predetermined ratio (e.g., about 0.3 times) of a maximum value among values of the digital sensing signals DRX as the valid data. For example, when the predetermined ratio is about 0.3, the digital sensing signal DRX having a value greater than a predetermined value (e.g., maximum value× 0.3) may be selected as the valid data. As described above, when the valid data is calculated based on the maximum value of the digital sensing signal DRX, since the valid data is capable of being calculated based on different moisture levels for each user US, accuracy of the valid data may be improved.

The area compensator 120 calculates a touch area based on the valid data among the digital sensing signals DRX.

Figure 11:
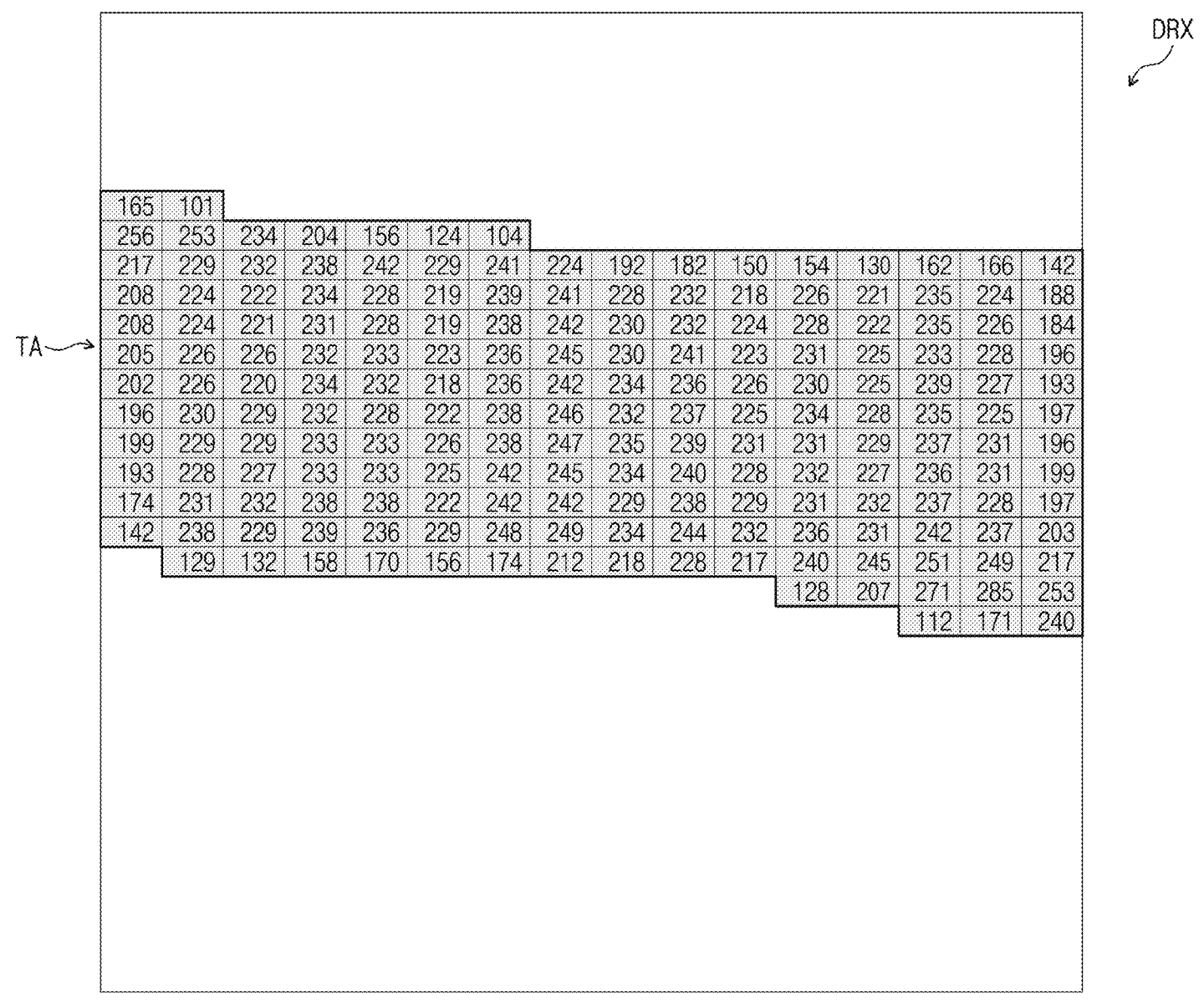

FIG. 11 is a view illustrating a touch area TA determined based on the valid data determined by the area compensator 110 according to an embodiment.

As illustrated in FIGS. 10 and 11, only a portion of the total sensing area SA may be detected as the touch area TA. The entire sensing area SA may be less than or equal to the image area DD-DA (refer to FIG. 8).

As described with respect to FIG. 6, the input sensor ISU may be a capacitive touch sensor. In an embodiment, the first sensing electrodes IE1-1 to IE1-5 receive a driving signal, and the second sensing electrodes IE2-1 to IE2-4 output a sensing signal corresponding to a change in capacitance between the first sensing electrodes IE1-1 to IE1-5 and the second sensing electrodes IE2-1 to IE2-4. For instance, one of the first sensing electrodes IE1-1 to IE1-5 and one of the second sensing electrodes IE2-1 to IE2-4 are capacitively coupled to each other to output one sensing signal RXS through a second signal line among the second signal lines SL2-1 to SL2-4.

As illustrated in FIG. 8, when a large area of the skin of the user US is in contact, the number of first sensing electrodes IE1-1 to IE1-5 capacitively coupled to one second sensing electrode among the second sensing electrodes IE2-1 to IE2-4 may be two or more. In this case, it may be difficult to accurately measure the moisture level.

The area compensator 120 may compensate the digital sensing signal DRX according to the touch area TA to improve the accuracy of the moisture level.

In an embodiment, the area compensator 120 may compensate the digital sensing signal DRX based on the number of valid data. In the example illustrated in FIG. 10, the entire sensing area SA includes 16×33=528 digital sensing signals DRX. In the example illustrated in FIG. 11, the touch area TA calculated based on the valid data includes 192 digital sensing signals DRX. In the examples illustrated in FIGS. 10 and 11, an area ratio TA/SA is about 192/528≈0.36.

Figure 12:
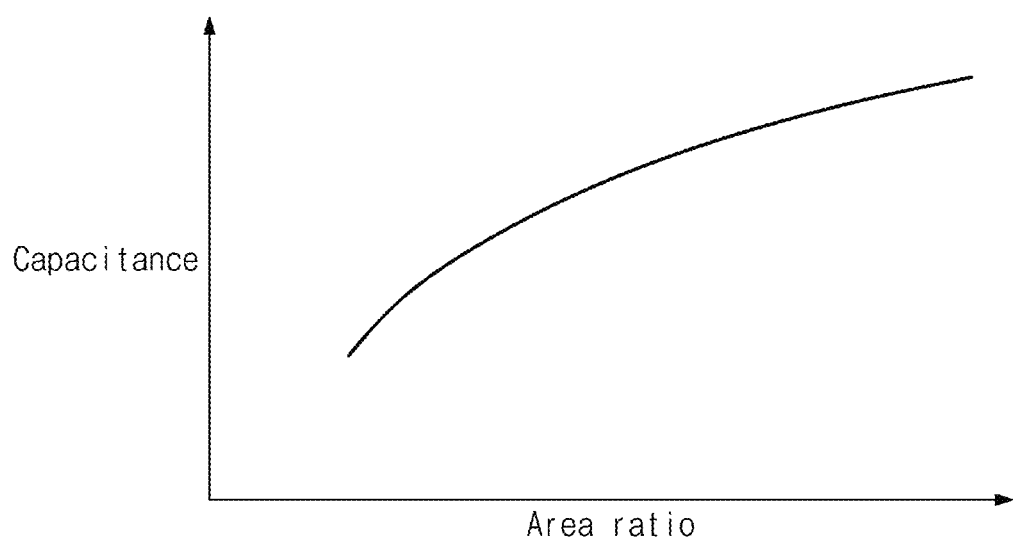
FIG. 12 is a graph illustrating a change in capacitance between a first sensing electrode and a second sensing electrode according to an area ratio according to an embodiment.

FIG. 12 is a graph illustrating a change in capacitance between the first sensing electrode and the second sensing electrode according to the area ratio according to an embodiment.

As illustrated in FIG. 12, it may be that as the area ratio increases, e.g., as the ratio of the touch area TA to the total sensing area SA increases, capacitance of the first sensing electrode and the second sensing electrode also increases. In an embodiment, when a value obtained by subtracting the compensation value from the digital sensing signal DRX is referred to as the compensation signal CRX, the compensation value may increase as the area ratio increases.

Referring again to FIG. 9, the area compensator 120 may output the compensation signal CRX that compensates for the digital sensing signal DRX according to the ratio of the touch area TA to the entire sensing area SA.

The representative value extracting part 130 extracts a representative value RV from the compensation signal CRX corresponding to the touch area TA (refer to FIG. 11). The selected representative value RV is a value representing the skin moisture level of the user US (refer to FIG. 8) among the compensation signals CRX corresponding to the touch area TA.

In an embodiment, the representative value RV may be one of a mean value, a median value, and a mode value of the compensation signal CRX corresponding to the touch area TA (refer to FIG. 11). In an embodiment, the representative value RV may be calculated (or determined) by an equation calculated based on statistical data, which is a result of measuring the skin moisture level of a population (e.g., a representative population), and the compensation signal CRX.

In an embodiment, the representative value RV may be set differently according to the position of the skin (e.g., the face, the arm, the abdomen, etc.) that the user US uses for sensing the moisture level. Also, the representative value RV may be set differently according to the gender (e.g., female or male) of the user US.

The moisture level calculator 140 outputs a moisture level signal M_DATA based on the representative value RV output from the representative value extracting part 130. In an embodiment, the representative value RV and the moisture level signal M_DATA may have a proportional relationship. For instance, the greater the representative value RV, the higher the moisture level signal M_DATA. The moisture level signal M_DATA may be a value within a preset range in an embodiment. In an embodiment, the moisture level signal M_DATA may be output as a value between 0 and 100.

Figure 13:
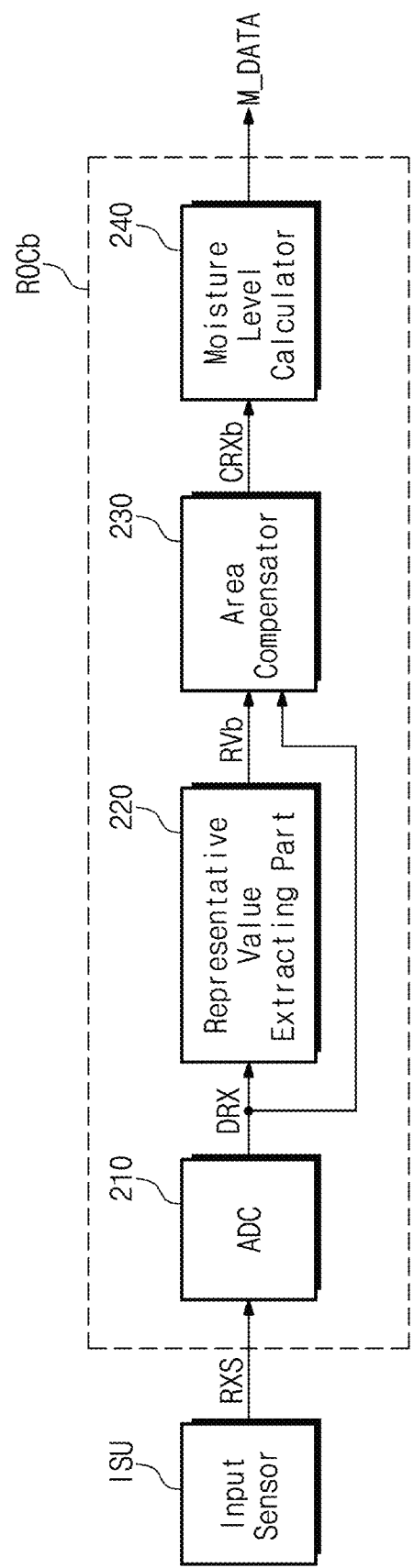
FIG. 13 is a block diagram illustrating a configuration of a readout circuit according to an embodiment.

FIG. 13 is a block diagram illustrating a configuration of a readout circuit according to an embodiment.

Referring to FIG. 13, a readout circuit ROCb may include an analog-to-digital converter 210, a representative value extracting part 220, an area compensator 230, and a moisture level calculator 240.

The readout circuit ROC illustrated in FIG. 9 may performs area compensation for a digital sensing signal DRX output from the analog-to-digital converter 110 in advance and then extract a representative value RV.

The representative value extracting part 220 of the readout circuit ROCb illustrated in FIG. 13 extracts a representative value RVb based on the digital sensing signal DRX output from the analog-to-digital converter 210. The representative value RVb may be one of a mean value, a median value, and a mode value of the digital sensing signal DRX. In an embodiment, the representative value RVb may be determined (e.g., calculated) by an equation calculated based on statistical data, which is a result of measuring a skin moisture level of a population (e.g., a representative population), and the digital sensing signal DRX.

The area compensator 230 determines a touch area TA based on the digital sensing signal DRX. The area compensator 230 may output the compensation signal CRXb that compensates for the representative value RVb according to a ratio of the touch area TA to an entire sensing area SA.

The moisture level calculator 240 outputs the moisture level signal M_DATA based on the compensation signal CRXb output from the area compensator 230. In an embodiment, the compensation signal CRXb and the moisture level signal M_DATA may have a proportional relationship.

Figure 14:
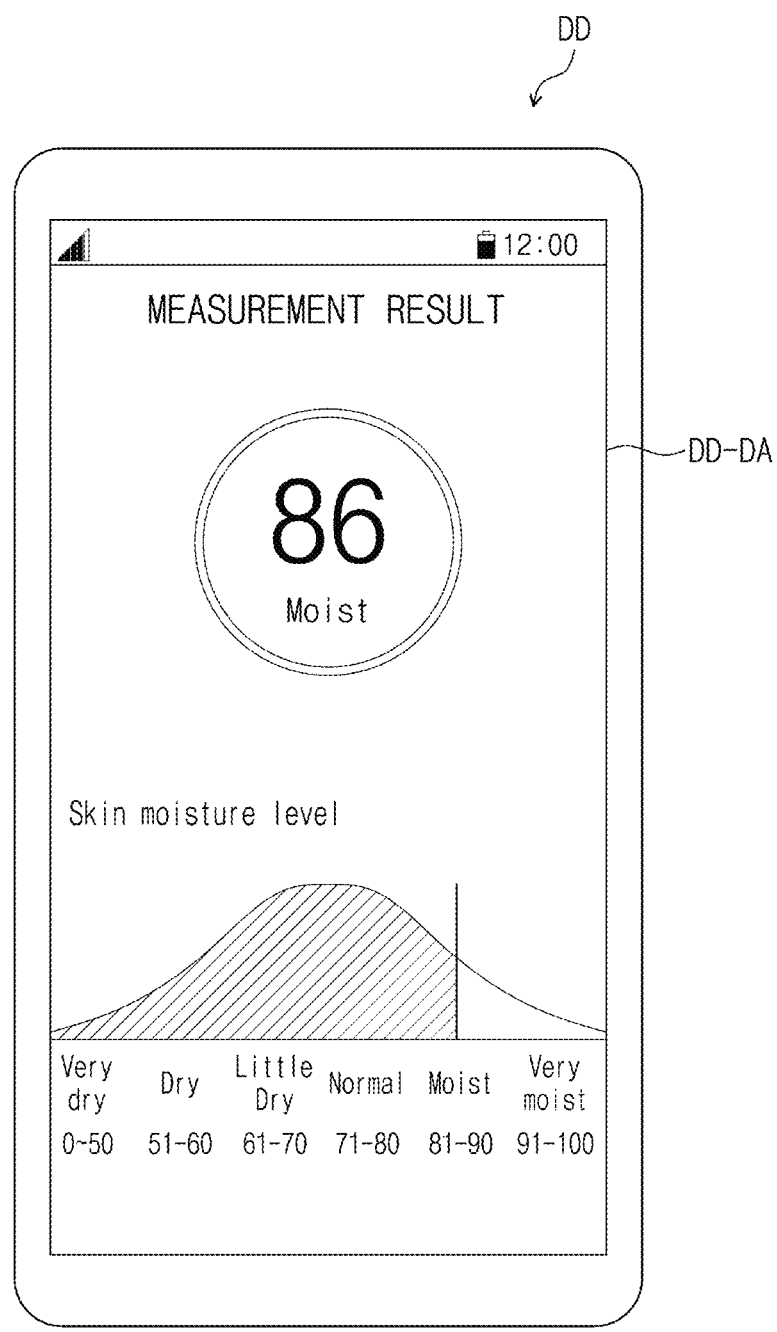
FIG. 14 is a view illustrating results obtained by measuring a moisture level according to an embodiment.

FIG. 14 is a view illustrating results obtained by measuring a moisture level according to an embodiment.

Referring to FIGS. 9 and 14, the display device DD may display an image, which corresponds to the moisture level signal M_DATA output from the readout circuit ROC, on an image area DD-DA.

In an embodiment, the readout circuit ROC may provide the moisture level signal M_DATA to the panel driving circuit PDC (refer to FIG. 2). The panel driving circuit PDC controls an image corresponding to the moisture level signal M_DATA to be displayed on the active area AA of the display panel DP. The image displayed on the active area AA of the display panel DP may be displayed on the image area DD-DA of the display device DD. The user US may easily know his/her skin moisture level with the image displayed on the display device DD.

Figure 15:
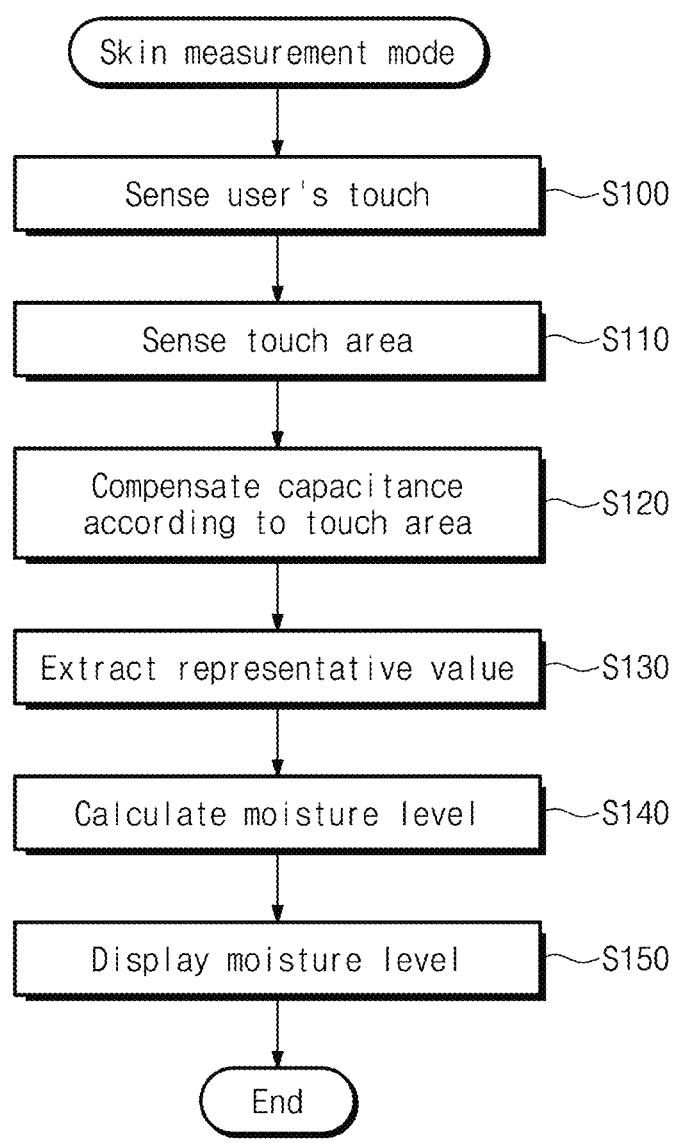
FIG. 15 is a flowchart illustrating an operation of a display device according to an embodiment.

FIG. 15 is a flowchart illustrating an operation of the display device according to an embodiment.

Referring to FIGS. 8, 9, and 15, the display device DD may display a message on an image area DD-DA in a skin measurement mode (or moisture level measurement mode). The display device DD displays, for example, a message "Please contact the skin on the screen" on the image area DD-DA. The user US may allow the skin to be in contact with the display device DD according to the message.

The readout circuit ROC senses a touch (contact) of the user US by receiving a sensing signal RXS (operation S100). When the touch of the user US is sensed, the input sensor ISU outputs a sensing signal RXS to an analog-to-digital converter 110. The analog-to-digital converter 110 converts the sensing signal RXS into a digital sensing signal DRX.

The area compensator 120 senses the touch area TA (refer to FIG. 11) based on the digital sensing signal DRX (operation S110). The touch area TA may be a contact area between a portion of the user's body and the input sensor ISU. If the user's touch area TA is less than a reference area, the display device DD may display a message requesting that the user US be in contact with the image area DD-DA again.

The area compensator 120 outputs a compensation signal CRX that performs capacitance compensation according to the touch area (operation S120).

The representative value extracting part 130 extracts a representative value RV from a compensation signal CRX corresponding to the touch area TA (refer to FIG. 11) (operation S130).

The moisture level calculator 140 outputs a moisture level signal M_DATA based on the representative value RV output from the representative value extracting part 130 (operation S140).

The panel driving circuit PDC (refer to FIG. 2) of the display device DD is controlled so that an image corresponding to the moisture level signal M_DATA (for example, the image illustrated in FIG. 14) is displayed on the active area AA of the display panel DP (operation S150).

Figure 16:
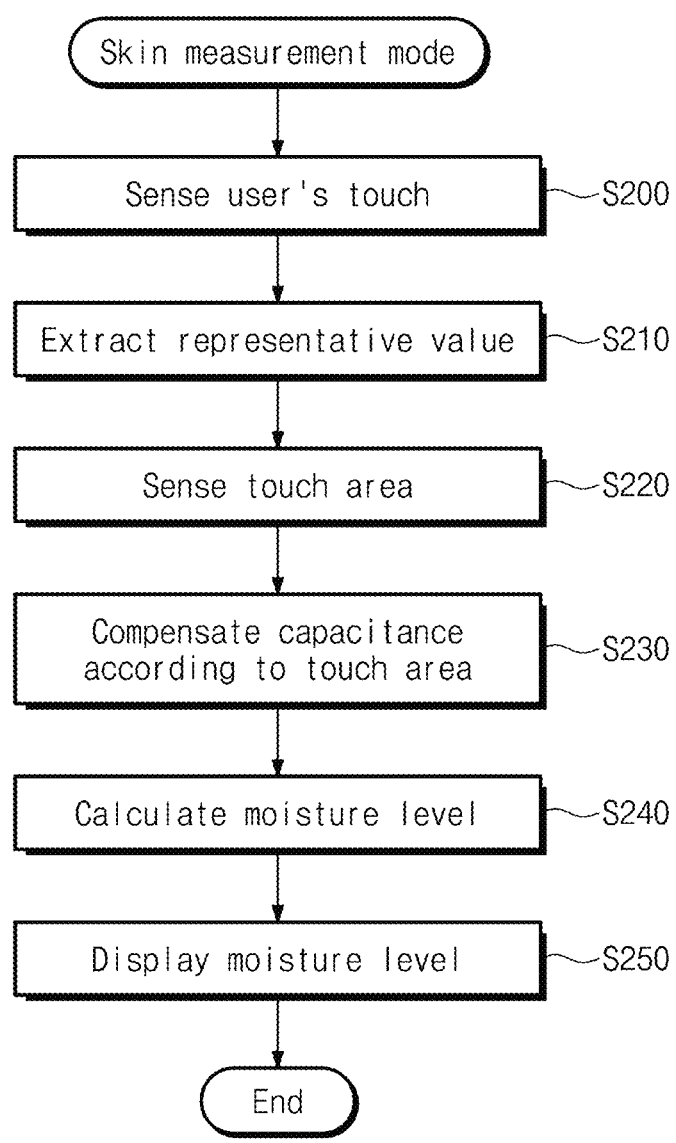
FIG. 16 is a flowchart illustrating an operation of a display device according to an embodiment.

FIG. 16 is a flowchart illustrating an operation of the display device according to an embodiment.

Referring to FIGS. 8, 13, and 16, the display device DD may display a message on an image area DD-DA in a skin measurement mode. The display device DD displays, for example, a message "Please contact the skin on the screen" on the image area DD-DA. The user US may allow their skin to be in contact with the display device DD according to the message.

The readout circuit ROCb senses a touch (contact) of the user US by receiving a sensing signal RXS (operation S200). When the touch of the user US is sensed, the input sensor ISU outputs a sensing signal RXS to an analog-to-digital converter 210. The analog-to-digital converter 210 converts the sensing signal RXS into a digital sensing signal DRX.

The representative value extracting part 220 extracts a representative value RVb from the digital sensing signal DRX output from the analog-to-digital converter 210 (operation S210).

The area compensator 230 senses the touch area TA (refer to FIG. 11) based on the digital sensing signal DRX (operation S220). The touch area TA may be a contact area between a portion of the user's body and the input sensor ISU. If the user's touch area TA is less than a reference area, the display device DD may display a message requesting that the user US be in contact with the image area DD-DA again.

The area compensator 230 may output the compensation signal CRXb that compensates for the representative value RVb according to a ratio of the touch area TA to an entire sensing area SA (operation S230).

The moisture level calculator 240 outputs the moisture level signal M_DATA based on the compensation signal CRXb output from the area compensator 230 (operation S240). In an embodiment, the compensation signal CRXb and the moisture level signal M_DATA may have a proportional relationship.

The panel driving circuit PDC (refer to FIG. 2) of the display device DD is controlled so that an image corresponding to the moisture level signal M_DATA (for example, the image illustrated in FIG. 14) is displayed on the active area AA of the display panel DP (operation S250).

The display device having the above constituents may measure a user's skin moisture level and display the measured result on a display panel. Therefore, the convenience for the user's use of the display device may be improved.

Although certain embodiments and implementations have been described herein, other embodiments and modifications will be apparent from this description. Accordingly, the inventive concepts are not limited to such embodiments, but rather to the broader scope of the accompanying claims and various obvious modifications and equivalent arrangements as would be apparent to one of ordinary skill in the art.

What is claimed is:

1. A display device comprising:
a display panel configured to display an image;
an input sensor disposed on the display panel; and
a readout circuit configured to output a moisture level signal corresponding to sensing signals received from the input sensor in a skin measurement mode.

2. The display device of claim 1, wherein:
the input sensor is disposed directly on the display panel; and
wherein the input sensor comprises:
first sensing electrodes;
second sensing electrodes crossing the first sensing electrode;
first signal lines electrically connected to the first sensing electrodes, respectively; and
second signal lines electrically connected to the second sensing electrodes, respectively.

3. The display device of claim 2, wherein the readout circuit is configured to:
transmit a transmission signal to the first signal lines; and
receive the sensing signals from the second signal lines.

4. The display device of claim 2, wherein each of the first sensing electrodes and the second sensing electrodes has a mesh shape.

5. The display device of claim 2, wherein the readout circuit comprises:
an analog-to-digital converter configured to convert each of the sensing signals to a digital sensing signal;
an area compensator configured to determine a touch area based on the digital sensing signal and output a compensation signal for compensating capacitance according to the touch area;
a representative value extracting part configured to extract a representative value based on the compensation signal; and
a moisture level calculator configured to output the moisture level signal based on the representative value.

6. The display device of claim 5, wherein each of the sensing signals represents capacitance between one of the first sensing electrodes and one of the second sensing electrodes.

7. The display device of claim 5, wherein the area compensator is configured to:
select a portion of the sensing signals as valid data; and
determine the touch area based on the valid data.

8. The display device of claim 7, wherein the area compensator is further configured to select a sensing signal having a value greater than a predetermined ratio of a sensing signal having a maximum value among the sensing signals as the valid data.

9. The display device of claim 7, wherein the area compensator is further configured to output the compensation signal corresponding to the capacitance compensation based on a number of valid data among the sensing signals.

10. The display device of claim 5, wherein the representative value comprises one of a mean value, a median value, and a mode value of the compensation signal within the touch area.

11. The display device of claim 2, wherein the readout circuit comprises:
an analog-to-digital converter configured to convert each of the sensing signals to a digital sensing signal;
a representative value extracting part configured to extract a representative value based on the digital sensing signal;
an area compensator configured to determine a touch area based the digital sensing signal and output a compensation signal corresponding to capacitance compensation according to the touch area on the representative value; and
a moisture level calculator configured to output the moisture level signal based on the compensation signal.

12. The display device of claim 11, wherein each of the sensing signals represents capacitance between one of the first sensing electrodes and one of the second sensing electrodes.

13. The display device of claim 11, wherein the area compensator is configured to:
select a sensing signal having a value greater than a predetermined ratio of a sensing signal having a maximum value among the sensing signals as valid data; and
determine the touch area based on the valid data.

14. The display device of claim 13, wherein the area compensator is configured to output the compensation signal corresponding to the capacitance compensation based on a number of valid data among the sensing signals.

15. A method for operating a display device, the method comprising:
receiving sensing signals from an input sensor;
sensing a touch area based on the sensing signals;
outputting a compensation signal corresponding to capacitance compensation according to the touch area;
extracting a representative value based on the compensation signal;
outputting a moisture level signal based on the representative value; and
causing, at least in part, an image corresponding to the moisture level signal to be displayed on a display panel.

16. The method of claim 15, wherein the input sensor comprises:
first sensing electrodes;
second sensing electrodes crossing the first sensing electrodes;
first signal lines respectively connected to the first sensing electrodes; and
second signal lines respectively connected to the second sensing electrodes, wherein each of the sensing signals represents capacitance between one of the first sensing electrodes and one of the second sensing electrodes.

17. The method of claim 15, wherein the sensing of the touch area comprises:
selecting a portion of the sensing signals as valid data; and
determining the touch area based on the valid data.

18. The method of claim 17, wherein the sensing of the touch area further comprises:
selecting a sensing signal having a value greater than a predetermined ratio of a sensing signal having a maximum value among the sensing signals as the valid data.

19. A method for operating a display device, the method comprising:
receiving sensing signals from an input sensor;
extracting a representative value based on the sensing signals;
sensing a touch area based on the sensing signals;
outputting a compensation signal corresponding to capacitance compensation according to the touch area based on the representative value;
outputting a moisture level signal based on the compensation signal; and
causing, at least in part, an image corresponding to the moisture level signal to be displayed on a display panel.

20. The method of claim 19, wherein the sensing of the touch area comprises:
selecting a portion of the sensing signals as valid data; and
determining the touch area based on the valid data.

\* \* \* \* \*